(12) United States Patent
Parker

(10) Patent No.: US 7,303,580 B2
(45) Date of Patent: Dec. 4, 2007

(54) STENT DELIVERY SYSTEM ALLOWING CONTROLLED RELEASE OF A STENT

(75) Inventor: Fred T. Parker, Unionville, IN (US)

(73) Assignee: Cook Incorporated, Bloomington, IN (US)

( * ) Notice: Subject to any disclaimer, the term of this patent is extended or adjusted under 35 U.S.C. 154(b) by 292 days.

(21) Appl. No.: 10/899,502

(22) Filed: Jul. 26, 2004

(65) Prior Publication Data

US 2006/0020321 A1    Jan. 26, 2006

(51) Int. Cl.
*A61F 2/06* (2006.01)
(52) U.S. Cl. .................... 623/1.11; 623/1.3
(58) Field of Classification Search ............. 623/1.11, 623/1.2, 1.15, 1.3
See application file for complete search history.

(56) References Cited

U.S. PATENT DOCUMENTS

| | | | |
|---|---|---|---|
| 4,768,507 A | 9/1988 | Fischell et al. | |
| 5,026,377 A | 6/1991 | Burton et al. | 606/108 |
| 5,409,495 A | 4/1995 | Osborn | 606/108 |
| 5,484,444 A | 1/1996 | Braunschweiler et al. | |
| 5,607,466 A | 3/1997 | Imbert et al. | |
| 5,702,418 A | 12/1997 | Ravenscroft | |
| 5,709,703 A | 1/1998 | Lukic et al. | |
| 5,733,325 A | 3/1998 | Robinson et al. | |
| 5,772,668 A | 6/1998 | Summers et al. | |
| 5,968,069 A | 10/1999 | Dusbabek et al. | 606/194 |
| 5,976,155 A | 11/1999 | Foreman et al. | |
| 6,077,295 A | 6/2000 | Limon et al. | |
| 6,077,297 A | 6/2000 | Robinson et al. | |
| 6,214,036 B1 | 4/2001 | Letendre et al. | |

(Continued)

FOREIGN PATENT DOCUMENTS

EP    1 400 219 A1    3/2004

OTHER PUBLICATIONS

International Search Report from corresponding PCT application No. PCT/US2005/025824, dated Nov. 10, 2005, 6 pages.

(Continued)

*Primary Examiner*—Anhtuan T. Nguyen
*Assistant Examiner*—Timothy J Neal
(74) *Attorney, Agent, or Firm*—Brinks Hofer Gilson & Lione

(57) ABSTRACT

A stent delivery system includes a stent having at least one eyelet and at least one rivet and a holder supporting the stent, wherein the holder includes a first section having a first diameter and a second section having a second diameter. A sheath covers the stent and the holder. The rivets are attached to each of the eyelets. A first inner diameter of the stent at the position of the rivets is smaller than a second inner diameter of the stent at other positions because the rivets protrude inwardly. A shoulder is formed on the holder due to the difference between the first diameter and the second diameter of the holder. The shoulder is positioned distally adjacent the rivets. The shoulder interferes with the protruding rivets, thereby restraining the longitudinal movement of the stent relative to the holder. Although the sheath is pulled back, the stent does not jump out of the stent delivery system. As a result, the stent delivery system allows the stent to be released in a controlled manner upon its deployment.

27 Claims, 2 Drawing Sheets

U.S. PATENT DOCUMENTS

| | | | |
|---|---|---|---|
| 6,267,783 B1 | 7/2001 | Letendre et al. | |
| 6,302,893 B1 | 10/2001 | Limon et al. | |
| 6,334,871 B1* | 1/2002 | Dor et al. | 623/1.34 |
| 6,350,278 B1 | 2/2002 | Lenker et al. | |
| 6,395,017 B1 | 5/2002 | Dwyer et al. | |
| 6,533,805 B1 | 3/2003 | Jervis | |
| 2002/0007206 A1 | 1/2002 | Bui et al. | |
| 2002/0049487 A1 | 4/2002 | Lootz et al. | |
| 2002/0120322 A1 | 8/2002 | Thompson et al. | |
| 2002/0120323 A1 | 8/2002 | Thompson et al. | |
| 2002/0143386 A1* | 10/2002 | Davila et al. | 623/1.15 |
| 2002/0161425 A1* | 10/2002 | Hemerick et al. | 623/1.11 |
| 2002/0193862 A1 | 12/2002 | Mitelberg et al. | |
| 2003/0023298 A1 | 1/2003 | Jervis | |
| 2003/0033001 A1 | 2/2003 | Igaki | |
| 2003/0040789 A1 | 2/2003 | Colgan et al. | |
| 2003/0060872 A1* | 3/2003 | Gomringer et al. | 623/1.15 |
| 2003/0074043 A1 | 4/2003 | Thompson | |
| 2004/0006380 A1* | 1/2004 | Buck et al. | 623/1.11 |
| 2004/0088039 A1* | 5/2004 | Lee et al. | 623/1.15 |

OTHER PUBLICATIONS

International Preliminary Report on Patentability for International Application No. PCT/US2005/025824 (8 pages).

* cited by examiner

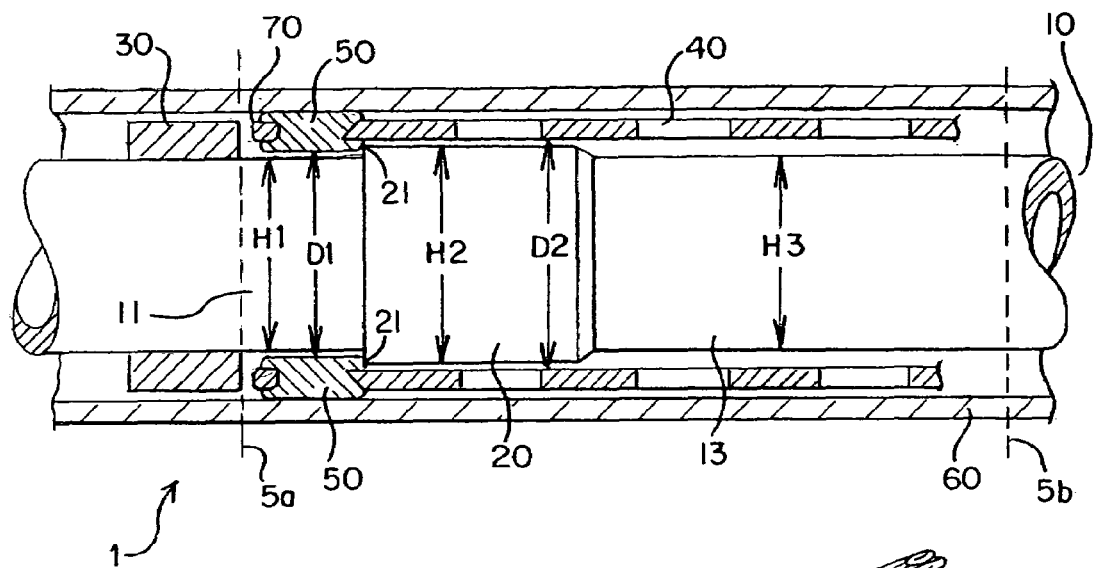
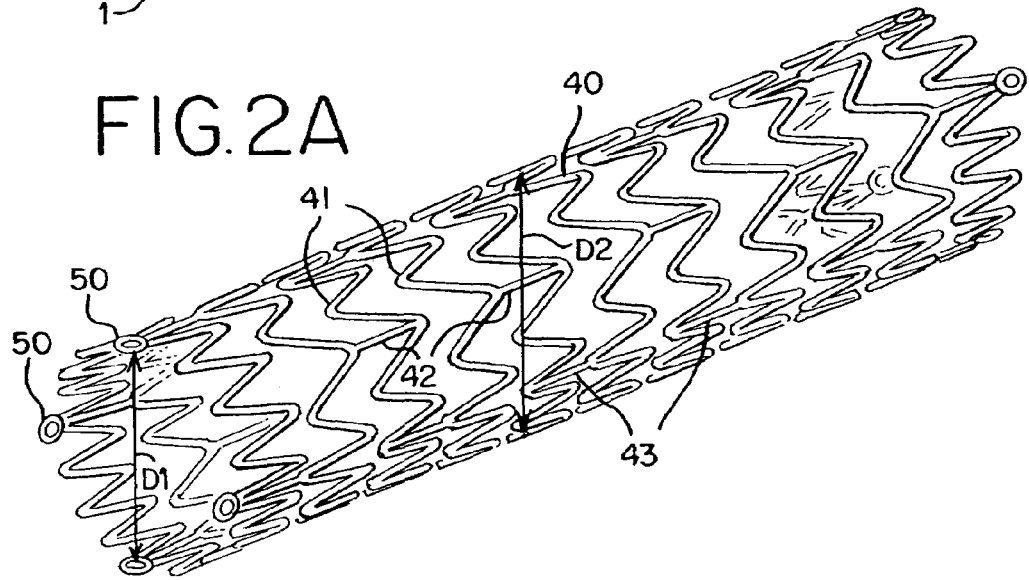
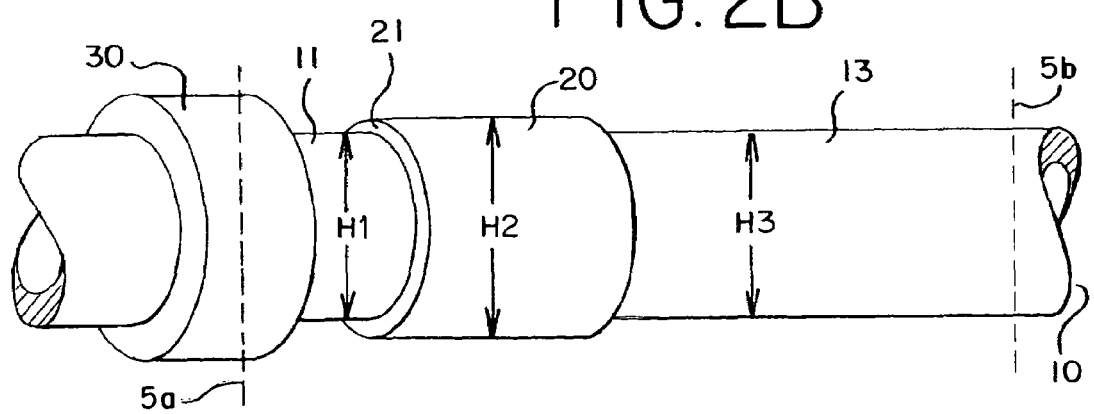

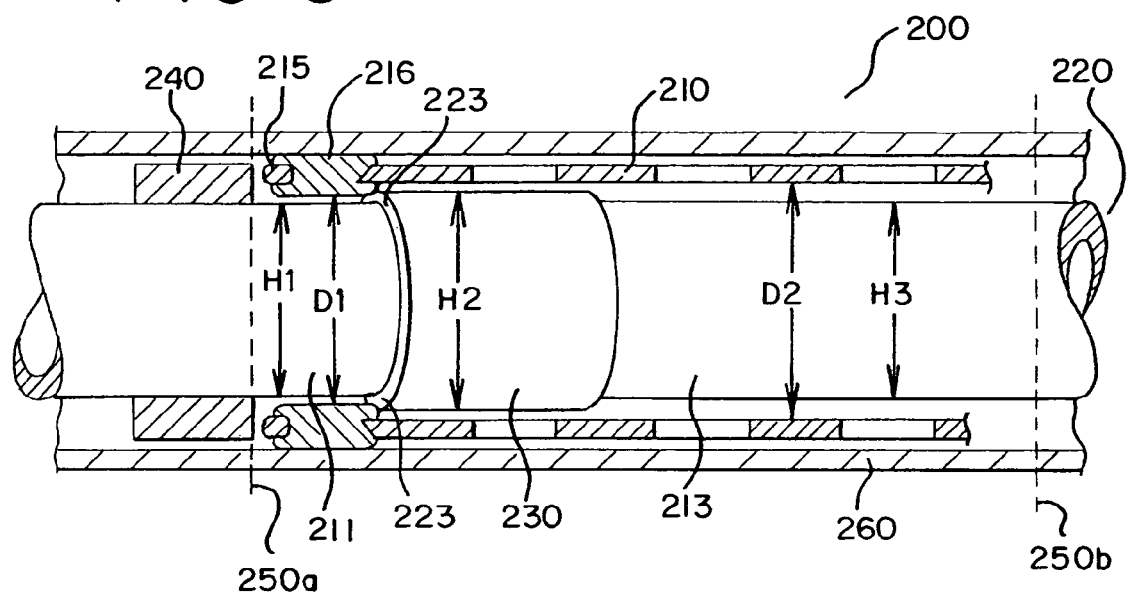
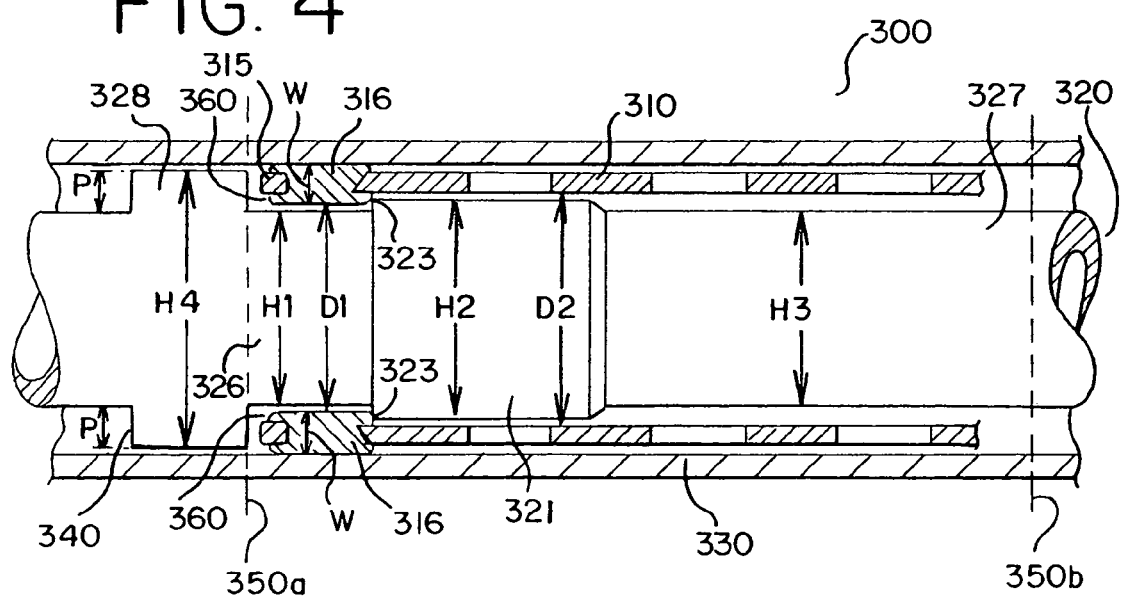

STENT DELIVERY SYSTEM ALLOWING CONTROLLED RELEASE OF A STENT

BACKGROUND OF THE INVENTION

1. Field of Invention

The present invention relates to a stent delivery system. More particularly, the present invention relates to a stent delivery system that allows a stent to be released in a controlled manner upon its deployment.

2. Description of the Prior Art

Stents are well known and widely used in medical procedures. Stents are frequently used to treat various organs and vessels in the vascular system. In particular, stents are most commonly used to treat vascular diseases using endovascular procedures. Patients who suffer from vascular diseases typically develop stenosis of various arteries, i.e., blood vessels that are clogged or narrowed by substances that restrict blood flow. Traditionally, operations such as bypass surgery have been performed to treat the stenosis of arteries. Bypass surgery involves opening of the chest cavity, which is a very invasive procedure for patients.

The development of fluoroscopy was one of the first uses of non-invasive medical procedures. Fluoroscopy allows medical personnel to see internal organs and blood vessels of a patient from outside of the patient's body. Fluoroscopy is typically performed by introducing a catheter into a bodily passageway of the patient, for example, through one of the vessels in the leg. The catheter is a surgical instrument for withdrawing fluid from or introducing fluid or various medical devices into the body of a patient. In fluoroscopy, contrast media is introduced into the vessel that is to be observed. The catheter and the contrast media used in such procedures are well known in the art and are only described here generally for background.

After the contrast media is introduced and delivered through the blood vessel of the patient, physicians are able to see the state of the vessel. By using X-ray, physicians are able to spot possible areas of stenosis in the blood vessel. Once a narrowed portion of a blood vessel is identified, a stent is introduced to the spot of the clogged or narrowed blood vessels in order to provide a structural support. The stent generally expands within the vessel until it contacts the vessel wall. However, if the stenosis of the vessel is particularly acute, for example, greater than fifty percent, or if the substance causing the stenosis is calloused, the stent may not be able to fully expand. In those situations, a balloon is inserted to predilate the vessel. Upon implantation, the stent provides permanent structural support so that the blood vessel remains dilated. Using stents has the distinct advantage of providing both patients and physicians with a non-invasive method of treating problems of internal organs and blood vessels over traditional surgery.

Two types of the stents are generally employed: balloon-expandable stents and self-expandable stents. Although balloon-expandable stents have been used prior to introduction of the self-expandable stents, both types of the stents are currently used by physicians, depending on the area to be treated, the size of the vessel lumen, the state of the stenosis and the physician's experience and preference. For example, balloon-expandable stents are often preferable for treating critical arteries that are unlikely to experience pressure from external traumas. One of the advantages of balloon-expandable stents is that the implanted diameter of the stent can be precisely controlled. However, a disadvantage of balloon-expandable stents is that they can be catastrophically deformed when force from an external trauma is applied to the stent. As a result, the balloon-expandable stents are well suited for coronary vessels as opposed to peripheral vessels, which are frequently subject to external traumas.

With balloon-expandable stents, a balloon with a stent mounted thereon is introduced through a catheter and is inflated at the site of the narrowed vessel. The stent expands until it contacts and presses against the vessel wall. In contrast, self-expandable stents are capable of expanding without the use of a balloon. Self-expandable stents are generally made of spring metal, for example, nitinol or stainless steel. Spring metal used for making self-expandable stents typically has shape memory characteristics. Self-expandable stents are readily deformable by pressure applied thereto but return to their original shape like a spring after the pressure is removed.

Accordingly, a typical procedure for implanting a self-expandable stent is as follows. First, the stent is delivered to the vessel area to be treated through a catheter in a compressed or collapsed state. In order to keep the stent compressed during delivery, a stent delivery system having a sheath and a holder is used. In general, the sheath is an outer cover and the holder is located inside the sheath. The sheath and the holder typically have a tubular shape. The self-expandable stent is interposed between the sheath and the holder. The sheath applies pressure to the stent, thereby maintaining the stent in the collapsed state. The holder supports and carries the stent until it is released from the stent delivery system. The stent delivery system is loaded into the catheter and delivered to the vessel where the stent is to be deployed.

Second, once the stent is positioned at the area to be treated, the stent is implanted by releasing the stent from the delivery system. To release the stent, the sheath is retracted so that the stent is exposed to the vessel. A holder band is typically positioned at the proximal end of the stent. The holder band basically prevents the stent from moving rearward as the sheath is retracted. Because the sheath directly contacts and presses against the stent, the stent has a tendency to move backward as the sheath. Thus, the holder band can restrain such movement of the stent, thereby allowing the stent to be released as the sheath is retracted. Once the sheath is withdrawn, the stent is freed from pressure and starts to expand. After the stent fully expands, the stent delivery system and the catheter are removed from the vessel.

The description of balloon-expandable stents and self-expandable stents is provided for general background only. However, regardless of the type of the stent that is used, physicians have many different preferred procedures and variations for implanting stents. Further, the techniques used for implanting stents are still developing and changing. In addition, procedures usually associated with one type of the stent may also be used with different types of the stents.

During the process of deploying a stent, a conventional stent delivery systems have difficulty in properly positioning the stent. As described above, the sheath first retracts to expose the stent. During that process, the stent may act like a spring. As a result, the stent may jump out of the sheath and be starting to expand. This problem most commonly occurs where the stent is a short stent. Short stents may quickly expand before the sheath is fully retracted. Once the stent starts to expand, it is not possible to compress the stent back into the delivery system in order to reposition the stent. Also, it is difficult to adjust the position of the stent once the stent contacts the wall of the vessel. Accordingly, a stent delivery system is desirable that is able to release a stent in a controlled manner upon deployment.

Currently, most stent delivery systems on the market do not have a controlled release mechanism. Accordingly, physicians must exercise extreme caution by slowly deploying the stent so that the distal end of the stent has time to contact the vessel wall before the proximal end of the stent exits the sheath. This method is inherently unreliable and is susceptible to uncontrolled release of the stent during deployment.

In U.S. Patent Publication Nos. 2002/0120322 and 2002/0120323, a similar problem was addressed. In these patent publications, an interlock system that engages male interlock structures on the stent with female interlock structures on an inner tubular member is described. As shown in FIG. 6A of the Publications, the male interlock structures are positioned at the proximal and distal ends of the stent. The female interlock structures are formed to receive and be engaged with the male interlock structures. When the stent is in the collapsed state, the male and female interlock structures are coupled to each other.

When the sheath is retracted, the stent remains in the collapsed state until it is fully exposed. As the stent expands radially, the male interlock structures are free to radially move out of the female structures. By using this interlock system, it is possible to prevent the stent from moving longitudinally during expansion of the stent. However, this interlocking system adds extra costs in manufacturing the male and female interlocking structures. The male and female interlocking structures need to fit into each other accurately. Considering the size of the stent, the addition of male and female interlocking structures may require costly and burdensome processes. In addition, the stent may be subject to additional friction due to the interlocking structures. For example, if the interlocking structures are engaged with each other too tightly, the stent may be hindered from moving out of the stent delivery system.

U.S. Pat. No. 6,077,295 discloses a self-expandable stent delivery system. The system allows a physician to recapture a partially deployed stent. The physician can partially deploy the stent, and if the position of the stent is incorrect, the physician can manipulate control handles so that the sheath and the holder of the stent delivery system move axially in opposite directions. Specifically, the control handles can be manipulated so that the holder moves in a proximal direction, whereas the sheath moves in a distal direction. This system works on the assumption that it is possible to perform accurate manipulation of the control handles. However, it is uncertain that physicians can accurately manipulate the control handles once the stent is partially deployed. Thus, this system is still prone to errors in positioning the stent during deployment.

BRIEF SUMMARY OF THE INVENTION

By way of introduction only, a stent delivery system provides a stent and a holder supporting the stent. The stent and the holder are covered by a sheath. The stent, the holder and the sheath may have a tubular shape. The stent may be a self-expandable type. The stent delivery system is loaded into a catheter to be introduced into a patient's body and eventually to a blood vessel to be treated. When the stent delivery system is loaded, the stent is in a compressed state and is interposed between the holder and the sheath.

The stent may include at least one eyelet and at least one rivet attached to the eyelet. Each rivet protrudes inwardly, thereby making an inner diameter at the position of rivets smaller than an inner diameter at other positions of the stent. The holder may include at least one portion having an increased diameter. Because of the increased diameter, a circumferential surface of the portion is outwardly exposed and constitutes a shoulder. The shoulder is located distally adjacent each rivet. Each rivet overlaps and interferes with the shoulder. Thus, the stent is trapped by the shoulder of the holder.

Upon deployment of the stent, such trapping of the stent prevents the stent from jumping out of the stent delivery system. The stent remains within the stent delivery system until it is sufficiently deployed, even though the sheath is retracted and no pressure is applied to the stent. Accordingly, physicians can release the stent in a controlled manner.

One embodiment of a stent delivery system includes a holder having a bump (or a step) as an increased diameter portion. The bump is made of the same material as the holder and is integrally formed with the holder. A shoulder for the bump is a circumferential surface of the bump, which protrudes radially outwardly from the rest of the holder because of the increased diameter.

A second embodiment of a stent delivery system includes a holder having a sleeve. The sleeve may be made of the same material as the holder but it is a separate piece from the holder.

A third embodiment of a stent delivery system includes a holder having an integrated holder band. The holder is designed to have at least two increased diameter portions. One portion comprises a bump and the other portion comprises the holder band. A diameter of the holder band portion is generally larger than a diameter of the bump portion. The bump portion is positioned distally adjacent eyelets and rivets. Between the bump portion and the holder band, a groove is formed to receive the eyelets and the rivets.

Various designs, shapes and structures are available for a stent delivery system. The foregoing discussion of the embodiments has been provided only by way of introduction. Nothing in this section should be taken as a limitation on the following claims, which define the scope of the invention.

BRIEF DESCRIPTION OF THE DRAWINGS

FIG. 1 is a cross sectional view of a first embodiment of a stent delivery system.

FIG. 2A is a perspective view of a stent used in the first embodiment of the stent delivery system as shown in FIG. 1.

FIG. 2B is a perspective view of a holder used in the first embodiment of the stent delivery system as shown in FIG. 1.

FIG. 3 is a cross sectional view of a second embodiment of a stent delivery system.

FIG. 4 is a cross sectional view of a third embodiment of a stent delivery system.

DETAILED DESCRIPTION OF THE INVENTION

Referring now to the drawings, embodiments of a stent delivery system will be described. The following description is made only for explanation purposes and does not limit the scope of the claims.

FIG. 1 shows a first embodiment of a stent delivery system 1. The stent delivery system 1 comprises a sheath 60 and a holder 10. The sheath 60 and the holder 10 have a tubular shape and extend from a proximal end 5a to a distal end 5b. A holder band 30 is positioned at the proximal end 5a. A stent 40 is interposed between the sheath 60 and the holder 10. The stent 40 comprises at least one eyelet 70 and at least one rivet 50.

The sheath 60 applies pressure to the stent 40 so that the stent 40 remains in a collapsed state. The holder band 30 extends radially around the holder 10 as shown in FIGS. 1 and 2B. The holder band 30 may be made of any material but is preferably rigid and hard. The holder band 30 blocks a longitudinal movement of the stent 40 as the sheath 60 is pulled rearward. Thus, the holder band 30 prevents the stent 40 from moving along with the retracted sheath 60.

Preferably, the stent 40 is in a collapsed state during delivery as shown in FIG. 1. The stent 40 is a self-expanding stent. Upon deployment, the stent 40 expands to provide structural support for a blood vessel. Preferably, the stent 40 is made of nitinol, but can also be made of numerous other materials known in the art. The stent 40 is typically spring elastic and has a natural tendency to expand from the collapsed state. Once pressure is removed, the stent 40 returns to its original expanded shape. Thus, it is preferred that the stent 40 is made of metal having shape memory characteristics.

The stent 40 typically has a cylindrical shape. The stent 40 comprises a plurality of struts 41 as shown in FIG. 2A. The plurality of struts 41 are interconnected with each other to constitute a plurality of rows. Neighboring rows are connected by longitudinal supports 42. FIG. 2A shows the stent having four eyelets 70 at both the proximal end 5a and the distal end 5bs of the stent 40. Another longitudinal support 43 may connect another set of neighboring rows at a different angular position than longitudinal supports 42. The longitudinal supports 42, 43 interconnect the stent 40 along the length of the stent 40 between the proximal 5a and distal 5b ends.

Referring back to FIG. 1, the eyelets 70 and the rivets 50 of the stent 40 are shown. The eyelets 70 are hollow and preferably ring shaped. The eyelets 70 are filled with rivets 50. In other words, the eyelets 70 serves as a platform to receive the rivets 50 (FIG. 2A). The rivets 50 as shown in FIG. 1 are flat and have circular shapes. The rivets 50 are made of radiopaque material so that they function as markers during the implantation of the stent 40. Typically, the stent delivery system is not easily detectable by X-ray once it is introduced into the vessel of the patient. However, it is important for physicians to know the location of the stent delivery system during the implantation procedures so that they can accurately deploy the stent. Preferably, the rivets 50 are detectable by X-ray to provide the physician with a location indication. Although physicians may not see other parts of the stent delivery system, they can typically see the rivets 50 using X-ray visualization equipment. One of skill will readily understand the use of radiopaque markers and techniques that may be used to install the rivets into the eyelets of the stent.

Referring to FIGS. 1 and 2A, the stent 40 is collapsed onto the holder 10, and accordingly, the inner diameter of the stent 40 may be designed to be slightly larger than that of the holder 10, and the outer diameter may be smaller than that of the sheath 60. Specifically, the stent 40 has an outer diameter that is about the same as the inner diameter of the sheath 60. Typically, the outer diameter of the stent 40 is about 0.076 inch and the inner diameter of the sheath 60 is also about 0.076 inch. The sheath 60 directly contacts and presses against the outer surface of the stent 40. On the other hand, the inner diameter of the stent 40 is normally larger than the diameter of the holder 10.

The stent 40 comprises a first portion and a second portion having two different inner diameters. The first portion has a first inner diameter D1 and the second portion has a second inner diameter D2 as shown in FIG. 1. The first inner diameter D1 is smaller than the second inner diameter D2. The first portion of the stent 40 comprises the eyelets 70 and the rivets 50. For example, the stent 40 may have four eyelets 70 where the rivets 50 are attached to fill hollow portions of the eyelets 70 as shown in FIG. 2A. Turning back to FIG. 1, the first inner diameter D1 at the point where the rivets 50 are located is different from the second inner diameter D2 at the body of the stent 40. This difference in D1 and D2 derives from the construction of the eyelets 70 and rivets 50. In particular, the rivets 50 inwardly protrude from surfaces of the eyelets 70 where the each rivet is attached, thereby forming the smaller inner diameter D1. As a result, the first portion is where the eyelets 70 and rivets 50 are formed as the radiopaque marker, as shown in FIG. 1. The second portion is the rest of the stent body. In FIG. 2A, the stent 40 has another first portion at the distal end 5b.

The difference between D1 and D2 is relatively small and does not need to be particularly large. For example, D1 is about 0.054 inch, whereas D2 is about 0.060 inch. The difference between D1 and D2 is typically about 0.006 inch. However, the difference between D1 and D2 could be as small as 0.001~0.002 inch total. Alternatively, other values for D1 and D2 are possible.

In FIG. 1, the holder 10 includes a proximal section, i.e., a first section 11 having a first diameter H1 and a second section having a second diameter H2. The second section comprises a bump 20. FIG. 2B shows the second section 20 of the holder 10 is designed to comprise the bump 20 at the midsection of the stent body. The bump 20 may start from the midsection of the holder 10 and extend toward the eyelets 70. The holder 10 further comprises a distal section, i.e., a third section 13 having a third diameter H3 and disposed distally relative to the second section 20. The first diameter H1 and the third diameter H3 are smaller than the second diameter H2. The first diameter H1 is the same as, or alternatively, smaller than the third diameter H3. If the first diameter H1 and the third diameter H3 are the same, the holder 10 has the same diameter H1 or H3 throughout its body except the second section 20, i.e., the bump 20. Like the inner diameters D1, D2 of the stent 40 as above, the difference between diameters H1 and H2 of the holder are typically relatively small. For example, H1 may be as small as 0.053 inch and H2 may be about 0.059 inch. Accordingly, the difference between H1 and H2 is about 0.006 inch.

Because the stent 40 is radially collapsed onto the holder 10, the second diameter H2 of the holder is typically smaller than the second inner diameter D2 of the stent. The second diameter H2, however, could be the same as the second inner diameter D2, if the holder 10 and the stent 40 are made of material that permits a tight tolerance. In addition, the first diameter H1 of the holder 10 is generally smaller than the first inner diameter D1 of the stent. The second diameter H2 of the holder, however, is larger than the first inner diameter D1 and smaller than the second inner diameter D2, as shown in FIG. 1.

Referring again to FIG. 2B, the difference in the first and the second diameters H1 and H2 results in a radially exposed circumferential surface, or a shoulder 21. The shoulder 21 is about 0.006 inch total and about 0.003 inch per side in this embodiment. However, the shoulder may have different dimensions. As shown in FIG. 1, the shoulder 21 overlaps and interferes with the first portion of the stent 40 (i.e., inner diameter D1). The overlapping distance is equal to the difference between the first inner diameter D1 and the second diameter H2 of the holder 10 and may be about 0.0025 inch per side. Thus, the shoulder 21 may directly contact the side edges of the rivets 50.

The dimensions for the diameters D1, D2, H1, H2 and the shoulder 21 are provided above for description purposes only. Various dimensions and materials for the holder 10 and the stent 40 are possible as long as there is interference between the shoulder 21 and a portion of the stent 40. Another consideration for the diameter of the stent 40 is that its first inner diameter D1 is preferably as large as possible (i.e., rivets inwardly protrude as little as possible) so that the stent 40 smoothly deploys from the delivery system. On the other hand, the rivets need to protrude inwardly a sufficient extent to provide interference with the shoulder 21.

The manner of using the stent delivery system 1 is now apparent. The catheter is introduced into the patient's vessel. The stent delivery system 1 is then moved along with the catheter until the vessel portion to be treated is reached. During the delivery, the stent 40 remains in the collapsed state as shown in FIG. 1. The sheath 60 applies the needed pressure on the stent 40 to keep the stent 40 in the collapsed state.

Upon deployment of the stent 40, the sheath 60 is slowly retracted and the stent 40 is exposed. The stent 40 does not jump out of the stent delivery system 1 because the eyelets 70 and rivets 50 of the stent 40 are trapped by the shoulder 21 of the bump 20. The rivets 50 partially or wholly overlap and interfere with the shoulder 21. As a result, the stent 40 is temporarily restrained from longitudinal movement relative to the holder 10, even though the sheath 60 is retracted and the stent 40 is no longer subject to complete constraint. The stent 40 remains within the delivery system 1 until it radially expands. Once the stent 40 sufficiently expands, the eyelets 70 and rivets 50 expand away from the first section 11 and the second section 21 of the holder 10. Thus, the first inner diameter D1 of the stent 40 becomes much larger than the second diameter H2 of the bump 20 upon expansion of the stent 40.

Based on the above, it is possible to release the stent 40 in a more controlled manner than conventional stent delivery systems. Physicians do not need to expend extra energy exercising extreme caution to slowly release the stent 40. Moreover, no additional structures or processes are required to accomplish the controlled release. Therefore, the stent delivery system 1 of this embodiment provides a cost effective and readily controllable stent delivery device. Furthermore, the stent delivery system does not add extra expenses to manufacturing and loading of the stent into the stent delivery system. The stent delivery system 1 simply requires the process of designing the bump 20 at the midsection of the holder 10. The differences between D1 and D2 of the stent 40 do not need any further manufacturing step or process. Therefore, manufacturing costs are substantially minimized.

Furthermore, the second diameter H2 may be designed to have a different value. A change of the second diameter H2 results in a change in the difference between the first inner diameter D1 of the stent 40 and the second diameter H2 of the holder 10, which directly affects the overlapping distance between the shoulder 21 and the rivet 50. Trapping effect of the rivets 50 by the shoulder 21 is changed and adjustable by simply changing the value of the second diameter H2. In addition, it is also possible to change the first inner diameter D1. The change of the first diameter D1 also results in a change of the overlapping distance between the shoulder 21 and the rivets 50, thereby affecting the trapping effect by the shoulder 21. Thus, the degree of trapping may be easily modified as desired.

FIG. 3 shows a second embodiment of a stent delivery system 200. The stent delivery system 200 includes a sheath 260, a stent 210 and a holder 220. The stent 210 has a first portion comprising eyelets 215 and rivets 216 attached to the eyelets 215. The first portion has a first inner diameter D1, which is smaller than a second inner diameter D2. The stent 210 has a second portion having the second inner diameter D2 as shown in FIG. 3. The holder 220 comprises a proximal section, i.e., a first section 211, a second section and a distal section, i.e., a third section 213. The first section 211 has a first diameter H1 and the second section has a second diameter H2, which is larger than H1. The third section 213 has a third diameter H3, which is smaller than or the same as the first diameter. The diameters H1, H2 and the inner diameters D1, D2 have small dimensions. A holder band 240 is positioned at a proximal end 250a to block the rearward movement of the stent 210 when the sheath 260 is retracted.

In the second embodiment, the second section comprises a sleeve 230. As shown in FIG. 3, the sleeve 230 extends around radially, preferably, the midsection of the holder 220 to provide the second diameter H2. The sleeve 230 is of the same material as the holder 220. The sleeve 230 is designed to provide a shoulder 223. The shoulder 223 is formed due to the difference between the first diameter H1 and the second diameter H2. The shoulder 223 is positioned distally adjacent the first portion of the stent 210, and in particular adjacent the rivets 216. Accordingly, the rivets 216 interfere with and are trapped by the shoulder 223, thereby restraining the longitudinal movement of the stent 210 relative to the holder 220. The overlapping distance between the rivets 216 and the shoulder 223 is equal to the difference between the first inner diameter D1 and the second diameter H2, which may be about 0.0025 inch per side. Once the stent 210 starts to be deployed, it radially expands. Upon radial expansion of the stent 210, the rivets 216 are no longer trapped by the shoulder 223.

Like the previous embodiment, the stent 210 does not jump out of the stent delivery system 200. The stent 210 remains in the collapsed state until it radially expands upon its deployment, and the stent 210 is allowed to be released in a controlled manner. The stent delivery system 200 provides additional advantages in that the second diameter H2 of the holder 220 is easily changeable by using a sleeve having a different diameter. As described above, a change in the second diameter H2 results in change in the trapping effect because the overlapping distance between the shoulder and the rivets is changed. The sleeve structure facilitates this process by providing a simplified way of changing shoulder 223 and the resulting trapping effect. FIG. 3 shows one sleeve 230 covering the holder 220 and supporting the rivets 216. Alternatively, two or more sleeves may be used if necessary.

A third embodiment of a stent delivery system 300 is shown in FIG. 4. The stent delivery system 300 includes a stent 310, a holder 320 and a sheath 330. The holder 320 includes a bump 321 and is designed to make the holder band 340 an integrated part. Accordingly, the holder 320 includes a proximal section, i.e., a first section 326, a second section having the bump 321, a distal section (i.e., a third section 327), and a holder band section (i.e., a fourth section 328), as shown in FIG. 4. The holder band 340 needs to have a distance (P) that is sufficient to receive eyelets 315 of the stent 310. Accordingly, the holder band section 328 has a diameter H4, which is larger than the two diameters H1 and H2, as shown in FIG. 4. As discussed above, the diameters H1 and H2 are about 0.053 and 0.059 inch, respectively. The diameter H4 is about 0.075 inch. Each distance P, as shown in FIG. 4, is typically 0.022 inch per side. The width W of each eyelet 315 is about 0.025~0.027 inch. The third diameter H3 is the same as or larger than the first diameter H1. The dimensions provided for H1, H2, P and W are exemplary only and may be larger or smaller than the described values.

Because the holder band 340 is formed as an integrated part of the holder 320, a groove 360 is disposed between the holder band 340 and the bump 321. The depth of the groove 360 is about the same as the distance P of the holder band 340 and is about 0.022 inch per side. As shown in FIG. 4, the eyelets 315 and the rivets 316 are positioned in each groove 360.

The holder band 340 is made of the same material as the holder 320. Any material, such as metal, plastic or polymer, which preferably provides rigid, hard characteristics, may be used. For example, tungsten or stainless steel is used to make the holder. Alternatively, other materials are possible for the holder 320 and the holder band 340. The stent delivery system 300 reduces additional manufacturing costs because the holder band 340 is readily made during the process of manufacturing the holder 320.

In this embodiment, the shoulder 323 traps the eyelets 315 and the rivets 316 upon the deployment of the stent 310. The shoulder 323 partially or wholly overlaps and interferes with the rivets 316. The overlapping length between the shoulder 323 and the rivets 316 is equal to the difference between the first inner diameter D1 of the stent 310 and the second diameter H2 of the holder 320. The difference between the first inner diameter D1 and the second diameter H2 is about 0.005 inch. Because of the trapping of the rivets 316 by the shoulder 323, longitudinal movement of the stent 310 relative to the holder 320 is temporarily restrained and the stent 310 is prevented from jumping out of the stent delivery system 300. Because the groove 360 receives the eyelets 315 and the rivets 316 on the opposite side of the shoulder 323, it may further contribute to the trapping effect. In addition, the second diameter H2 may be changed, which results in a change of the overlapping distance between the shoulder 323 and the rivets 316. The trapping effects may be further increased or decreased depending on changes of the overlapping length. In addition, the value of the first inner diameter D1 may be changed as well. The change of the first inner diameter D1 also affects the trapping effect. This makes it possible to modify the degree of trapping effect as desired. Because only changes to the diameters D1 and H2 are required, no additional costly or complex processes is necessary. Thus, it is possible to provide a stent delivery system that is cost-efficient and has a more controlled release than the conventional stents.

As described in connection with various embodiments, the invention provides a stent delivery system employing a difference between inner diameters of the stent. The difference in the inner diameters of the stent is utilized to trap a portion of the stent until the stent is fully deployed. Such trapping prevents the stent from jumping out of the stent delivery system when the stent is being deployed. Thus, the stent can be released in a controlled manner.

The stent delivery system includes a holder that is designed to have an increased diameter. The holder includes a bump portion having an increased diameter. Alternatively, the holder includes a sleeve extending radially around the holder or an integrated holder band. These structural designs are intended to increase the diameter of the holder for the purpose of trapping a portion of the stent.

Although various embodiments of the invention have been described in connection with a stent delivery system, the invention is not limited to the described embodiment of the stent delivery system. The invention may be applicable to other medical systems or methods that involve implantation of a device or structure like a stent. The application of the invention may be more useful if the device or structure has characteristics of self-expansion.

Various embodiments of the invention have been explained, but they do not represent the scope of the invention. For example, it is apparent to those having ordinary skill in the art that modification and change may be made with the invention. It is therefore intended in the appended claims to cover all such changes and modifications which fall within the true spirit and scope of the invention.

I claim:

1. A stent delivery system, comprising:
   a generally cylindrical stent expandable from a collapsed state to an expanded state, the stent comprising a first portion having a first inner diameter and a second portion having a second inner diameter, the first inner diameter being smaller than the second inner diameter wherein the difference between the first inner diameter and the second inner diameter of the stent is the same in both the collapsed state and the expanded state; and,
   a generally cylindrical holder comprising a first section having a first diameter and a second section having a second diameter, the first diameter being smaller than the second diameter, wherein a shoulder is formed between the first section and the second section of the holder, the shoulder being disposed distally adjacent the first portion of the stent; and,
   wherein the stent is collapsed onto the holder, the second diameter of the holder being larger than the first inner diameter of the collapsed stent and smaller than the second inner diameter of the collapsed stent, the shoulder overlapping the first portion of the stent.

2. The stent delivery system of claim 1, wherein the second section of the holder comprises a bump integrally formed with the holder.

3. The stent delivery system of claim 1, wherein the second section of the holder comprises a sleeve installed onto the holder.

4. The stent delivery system of claim 1, wherein the first portion of the stent comprises at least one eyelet and at least one rivet.

5. The stent delivery system of claim 1, wherein the first portion of the stent comprises at least one radiopaque marker.

6. The stent delivery system of claim 1, wherein a difference between the first inner diameter and the second inner diameter of the stent is less than about 0.006 inch.

7. The stent delivery system of claim 1, wherein the shoulder has a distance of less than 0.003 inch.

8. The stent delivery system of claim 1, wherein the first inner diameter of the stent is less than the second diameter of the holder by about 0.005 inch.

9. The stent delivery system of claim 1, wherein the first portion of the stent is in direct contact with the shoulder of the holder.

10. The stent delivery system of claim 1, wherein the holder further comprises a third section having a third diameter, the third diameter being smaller than the second diameter, wherein the third section is distally disposed relative to the second section.

11. The stent delivery system of claim 1, wherein the first portion of the stent comprises at least one eyelet and at least one rivet, and the second section of the holder comprises a bump integrally formed with the holder.

12. The stent delivery system of claim 1, wherein the first portion of the stent comprises at least one eyelet and at least one rivet, and the second section of the holder comprises a sleeve installed onto the holder.

13. The stent delivery system of claim 1, wherein the first portion of the stent is in direct contact with the shoulder of the holder and the second section of the holder comprises a bump integrally formed with the holder.

14. A stent delivery system, comprising:
a generally cylindrical stent expandable from a collapsed state to an expanded state, the stent comprising a first portion having a first inner diameter and a second portion having a second inner diameter, the first inner diameter being smaller than the second inner diameter wherein the difference between the first inner diameter and the second inner diameter of the stent is the same in both the collapsed state and the expanded state; and,
a generally cylindrical holder comprising a first section having a first diameter, a second section having a second diameter, a third section having a third diameter and a fourth section having a fourth diameter, the first diameter being smaller than the second diameter, the second diameter being smaller than the fourth diameter and the third diameter being smaller than the second diameter and the third section disposed distally adjacent the second section, wherein a shoulder is formed between the first section and the second section and a groove is formed by the first section, the second section and the fourth section; and,
wherein the stent is collapsed onto the holder, the second diameter of the holder being larger than the first inner diameter of the collapsed stent and smaller than the second inner diameter of the collapsed stent and the shoulder is disposed distally adjacent the first portion of the stent and overlapping the first portion of the stent, thereby temporarily restraining a longitudinal movement of the stent relative to the holder.

15. The stent delivery system of claim 14, wherein the stent further comprises at least one eyelet and at least one rivet, the eyelet and the rivet forming the first portion of the stent and being disposed in the groove.

16. The stent delivery system of claim 14, wherein the stent further comprises at least one radiopaque marker, the radiopaque marker forming the first portion of the stent and being disposed in the groove.

17. The stent delivery system of claim 14, wherein the second section of the holder comprises a bump integrally formed with the holder.

18. The stent delivery system of claim 14, wherein the second section of the holder comprises a sleeve installed onto the holder.

19. The stent delivery system of claim 14, wherein the first inner diameter of the stent is less than the second diameter of the holder by about 0.005 inch.

20. The stent delivery system of claim 14, wherein the shoulder has a distance of less than about 0.003 inch.

21. The stent delivery system of claim 14, wherein a difference between the first inner diameter and the second inner diameter of the stent is less than about 0.006 inch.

22. The stent delivery system of claim 14, wherein the fourth section of the holder comprises a holder band integrally formed with the holder.

23. The stent delivery system of claim 14, wherein the first portion of the stent is in direct contact with the shoulder of the holder.

24. The stent delivery system of claim 14, wherein the stent further comprises at least one eyelet and at least one rivet, the eyelet and the rivet forming the first portion of the stent and being disposed in the groove and the second section of the holder comprises a bump integrally formed with the holder.

25. The stent delivery system of claim 14, wherein the stent further comprises at least one eyelet and at least one rivet, the eyelet and the rivet forming the first portion of the stent and being disposed in the groove and the second section of the holder comprises a sleeve installed onto the holder.

26. The stent delivery system of claim 14, wherein the stent further comprises at least one eyelet and at least one rivet, the eyelet and the rivet forming the first portion of the stent and being disposed in the groove and the fourth section of the holder comprises a holder band integrally formed with the holder.

27. The stent delivery system of claim 14, wherein the first portion of the stent is in direct contact with the shoulder of the holder and the second section of the holder comprises a bump integrally formed with the holder.

* * * * *